United States Patent [19]

Yuasa et al.

[11] Patent Number: 4,759,630
[45] Date of Patent: Jul. 26, 1988

[54] LAMP QUALITY JUDGEMENT APPARATUS AND JUDGEMENT METHOD THEREFOR

[75] Inventors: Kunio Yuasa, Yokohama; Haruo Sugiyama, Yokohama; Masao Nagai, Yokohama; Kunihiko Kihara, Kanuma; Takao Akaishi; Yasushi Tsujihara, both of Yokosuka, all of Japan

[73] Assignee: Kabushiki Kaisha Toshiba, Kawasaki, Japan

[21] Appl. No.: 891,132

[22] Filed: Jul. 31, 1986

[30] Foreign Application Priority Data

Jul. 31, 1985 [JP] Japan ................................ 60-167394
Feb. 20, 1986 [JP] Japan ................................ 61-33874
Feb. 26, 1986 [JP] Japan ................................ 61-39113

[51] Int. Cl.$^4$ .............................................. H01K 3/00
[52] U.S. Cl. .................................. 356/425; 356/311; 209/577
[58] Field of Search ............... 209/577, 578; 356/311, 356/425

[56] References Cited

U.S. PATENT DOCUMENTS 3,194,110 7/1965 Eppig et al. ........................ 209/577

FOREIGN PATENT DOCUMENTS 56-117465 9/1981 Japan .

OTHER PUBLICATIONS

IES Technial Paper No. 44, (1981): H. J. Eppig, "Appraisal of Incandescent Lamp Filling Gas Purity".

Primary Examiner—Edward P. Westin
Assistant Examiner—Khaled Shami
Attorney, Agent, or Firm—Oblon, Fisher, Spivak, McClelland & Maier

[57] ABSTRACT

The invention is a lamp quality judgement apparatus and judgement method which judge quality by detecting the state of gas sealed in an electric lamp such as a gas-filled incandescent lamp, etc. in which gas with an Argon-Nitrogen mixture as its main component is sealed. More particularly, a lamp in which such gas is sealed is classified as a good product or as a bad product by imposing a high DC voltage or a high AC or pulsed voltage with a comparatively low frequency of 1 kHz or less across the lamp's valve and filament coil to produce discharge and emission, in the lamp, of a light in a wavelength region in the vicinity of 560 nm and judging the radiation state in this 560 nm light spectrum, i.e., the state of discharge in the lamp. The means employed for detecting the light spectrum radiation state include means for judging lamp quality by monitoring the temporal response characteristic in the light spectrum in the 560 nm wavelength region and means for effecting accurate judgement of lamps regardless of variations in the state of discharge in lamps by detecting the difference in intensity of the light spectra of two wavelength regions which are the light spectrum of a 560 nm wavelength region and a light spectrum of a wavelength region other than the 560 nm wavelength region.

17 Claims, 9 Drawing Sheets

(b) 300 KHz

FIG. 9.

(a) GOOD PRODUCTS (b) SLIGHTLY DEFECTIVE PRODUCTS (c) MODERATELY DEFECTIVE PRODUCTS (d) BADLY DEFECTIVE PRODUCTS

(e) SEVERELY DEFECTIVE PRODUCTS

LAMP QUALITY JUDGEMENT APPARATUS AND JUDGEMENT METHOD THEREFOR

BACKGROUND OF THE INVENTION

1. Field of the Invention

The present invention relates to an automatic quality judgement apparatus and judgement method for lamps such as incandescent lamps, etc. More particularly, the invention relates to an automatic judgement apparatus and a judgement method in which the quality of a lamp is judged by detecting the state of gas that is sealed in the lamp.

2. Discussion of Background

Recent years have seen the development of high-speed automated lamp manufacturing equipment for automatic mass-production of a variety of types of lamps. In such a manufacturing process, in the case of incandescent lamps, for example, if evacuation of air is not effected satisfactorily in the course of the process or if the purity of the gas that has an inert gas such as Argon, etc. as its main component and is sealed in a lamp is low or if the sealing is unsatisfactory and slow leakage occurs, the filament breaks after only a short time of use (the life of the incandescent lamp becomes short) or there is reduction of the flux when the lamp emits light or there is deterioration of the flux maintenance characteristic, with the emitted light flux falling with elapse of light emission time. When such undesirable, defective lamps are manufactured, the defective products must be picked out and removed prior to shipment to the market.

There have been developed devices and methods for detecting the quality of incandescent lamps, i.e., for detecting whether or not admixture of air or moisture, etc. as well as Argon and Nitrogen gas has occurred due to improper sealing, without breaking the lamps.

For example, in a procedure conventionally employed in lamp manufacturing works to detect the state of gas in lamps and remove undesirable lamps during the lamp manufacturing process, a high frequency voltage is imposed on all the incandescent lamps that are manufactured to cause production of a discharge in the lamps and an operator removes lamps making a visual judgement of the color of the emitted light resulting from this discharge, so preventing shipment of the undesirable, defective incandescent lamps to the market.

Figure 15:
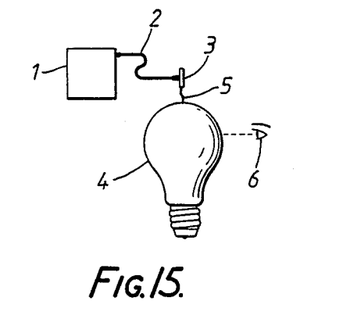
FIG. 15 is a model representation of a conventional example.

FIG. 15 shows an example of conventional operator-sorting. The high frequency voltage of a high frequency voltage generator 1 is supplied by a lead wire 2 to a discharge terminal 3, whereupon a high frequency discharge is produced between discharge terminal 3 and a filament or similar metal element not shown that is inside an incandescent lamp 4. The operator ascertains the state of the gas in incandescent lamp 4 and judges the quality of the product by observing, with the naked eye 6, the color of the radiated light and the form of the discharge at this time.

However, there has been a sharp increase in operators' wages and incandescent lamp manufacture has suddenly become a high-speed process recently, making it impossible for operators to keep up with the production speed by naked eye judgements as in this conventional procedure, and in view of these and similar factors there have been attempts to automate inspection.

Figure 16:
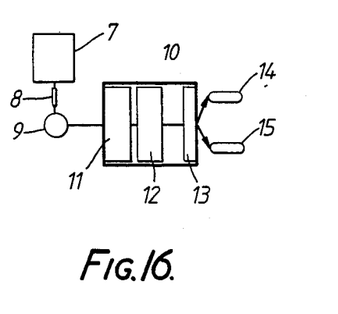
FIG. 16 is a block diagram of another conventional example.

An example of an automatic classification device is shown in FIG. 16. This is a device in which a sensor device 10 judges the light that is emitted when discharge occurs between the filament or other metal element inside an incandescent lamp 9 and a discharge terminal on which the high frequency voltage of a high frequency voltage generator 7 has been imposed. Sensor device 10 consists of a filter 11, photoelectric tube 12 and metering relay 13. When the discharge occurs, light, e.g., 360–420 nm light, which has passed through filter 11 is converted to a photoelectric current by photoelectric tube 12 and the voltage produced by causing this current to flow through a set load is supplied to metering relay 13. Incandescent lamps 9 for which the voltage is within a set range that has beeb set for metering relay 13 are taken to be passes and are forwarded to the next stage 14, while defective incandescent lamps 9 for which the voltage is outside this range are sent as rejects to a reject section 15.

In a conventional example such as this, however, there is the problem that it is difficult to detect whether products are good or not with a set filter for, e.g., 360–420 nm, because the discharge generation conditions vary.

A known example of a device such as this is that disclosed in Japanese Utility Model Disclosure No. 56-117465.

In more detail, a discharge terminal is brought near the outer wall of an incandescent lamp's bulb, glow discharge between the lamp's filament and the discharge terminal is produced by a high frequency voltage and the state of the sealed-in gas is judged on the basis of this glow discharge. Further, the quality of the lamp is determined through detection of the intensity of that portion of the light of the glow that is in the wavelength region 360–420nm.

With this technique, the quality of a lamp is judged on the basis of that light in the light spectrum produced by discharge which is in a wavelength region in which the intensity of the light varies in correspondence to the degree of defectiveness of the lamp, and the technique has the desirable aspect that the related configuration is made simple.

However, there is the drawback that reliable judgement is not possible, because the intensity in a specific light spectrum is detected and if, for example, the discharge inside lamps becomes unstable, this inevitably leads to a change in the light spectrum. Although it is desired to have a technical means for eliminating this drawback, all conventional techniques used judge lamp quality on the basis of intensity in a specific light spectrum and were therefore subject, in no small way, to adverse effects accompanying slight changes in the discharge phenomenon.

In view of this, the present inventors earlier developed an automatic incandescent lamp classification apparatus (Japanese Patent Application No. 60-167394) as follows.

It having been noted that although levels in a set wavelength region in the light spectrum produced accompanying incandescent lamp discharge when products are good are markedly different from the levels when products are deflective, the ratio of the intensity of light in this set wavelength region and the intensity of light in another region is practically unaffected and remains generally constant even if changes in level occur and can give improved classification performance, the apparatus uses the intensity ratio of the light in these two regions to judge the quality of incandescent lamps.

In the meantime, there has come to be a demand for still greater improvement of the classification performance of this apparatus, since today incandescent lamps are required to have extremely high reliability.

OBJECT OF THE INVENTION

The present invention has been devised in view of the above situation and has as its object to provide an automatic lamp classification apparatus which permits proper classification of good quality lamps and faulty lamps even in unstable conditions of discharge generation in lamps such as incandescent lamps, etc. It is a further object of the invention to provide a lamp classification method which makes it possible to achieve stable classification despite fluctuations in the discharge produced inside lamps.

SUMMARY OF THE INVENTION

To achieve these objects, what is done in the invention is to produce a discharge inside a lamp in which Argon-Nitrogen mixture gas or similar gas is sealed by imposing a high DC voltage (including pulse voltage) or a comparatively low frequency high AC voltage across its bulb and filament coil and to ascertain whether the lamp is a good product or a defective product by means of the spectrum of light with a wavelength in the vicinity of 560 nm (this is an approximate value, actually is 557 nm) that is radiated as a result of this discharge. This means the arrangement is one in which it is possible for good and defective lamp products to be distinguished with good discrimination performance even if changes in sensor output, etc. occur due to fluctuations in discharge states in lamps, changes in discharge states because of changes in lamp sizes or changes in the way the sensor is mounted, etc.

When the high voltage imposed on the lamp is a pulse current or alternating current voltage, the light in the 560 nm wavelength region constituting the parameter for judging lamp quality can be increased, and hence the judgement capability can be made still better, if it is imposed at a repetition frequency of 1 kHz or less.

Since the quality of lamps is judged by measuring the temporal response characteristic of the light spectrum in a wavelength region in the vicinity of 560 nm that is produced on occurrence of discharge caused by the high voltage imposed on the lamps, another object of the invention is to provide a lamp judgement method which gives a high judgement capability irrespective of changes in discharge production states inside lamps and fluctuations in light spectrum intensity that may occur.

A further object of the invention is to provide an automatic lamp quality judgement apparatus in which the judgement capability is improved by measuring light spectra with two different wavelengths.

It is an aspect of the invention that it was noted that in the case of incandescent lamps containing a sealed-in gas with a mixture of, for example, Argon gas and Nitrogen gas as its main component, within a set wavelength region, levels in the vicinity of 560 nm in the light spectrum produced accompanying incandescent lamp discharge when products are good are markedly different from the levels when products are defective but the ratio of the intensity of light in this set wavelength region and the intensity of light in another region is practically unaffected and remains generally constant even if changes in level occur and can give improved classification performance, and the invention uses this intensity ratio to judge the quality of incandescent lamps.

The invention also provides an automatic incandescent lamp classification apparatus which comprises a discharge generator which produces a discharge by imposing a high voltage that is repeated at 1 kHz or less on a incandescent lamp and a judgement device which judges whether the lamp is a good product or a defective product on the basis of the intensity of the intensity ratio of the light of at least two wavelength regions, which are that light of a set wavelength region in the spectrum of light emitted during the discharge for which the output is varied in correspondence to the state of gas in the incandescent lamp and light of another wavelength region whose output does not vary so much. This apparatus offers still better classification capability, since use of a high voltage that is repeated at a frequency of 1 kHz or less increases the light of the set wavelength region that constitutes a parameter for judging incandescent lamp quality.

As described above, the invention comprises a discharge generator which produces a discharge by imposing a high voltage that is repeated at 1 kHz or less on a incandescent lamp and a judgement device which judges good and defective incandescent lamp products on the basis of the intensity of the intensity ratio of the light of at least two wavelength regions, which are that light of a set wavelength region in the spectrum of light emitted during the discharge for which the output is varied in correspondence to the state of gas in the incandescent lamp and light of another wavelength region whose output does not vary so much.

The invention thus makes it possible to increase the light in a set wavelength region which constitutes a parameter for classification of incandescent lamp quality and to distinguish between good and defective incandescent lamp products with good precision on the basis of the intensity ratio of light in at least two wavelength regions, the increased light of the set wavelength region and light of another wavelength region. In other words, classification of product quality is effected accurately and surely and the classification capability is greatly increased thanks to an increase in the light of a set wavelength region that constitutes a parameter of incandescent lamp quality.

DETAILED DESCRIPTION OF THE PREFERRED EMBODIMENTS

There now follows a detailed description of embodiments of the apparatus and lamp classification method of the invention given with reference to the drawings.

Figure 1:
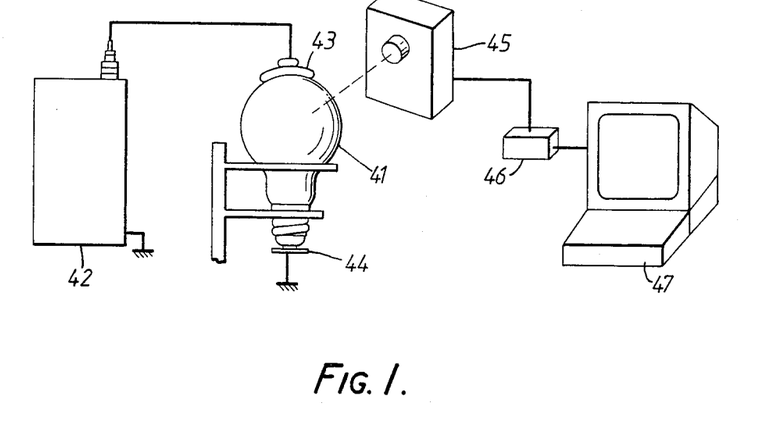
FIG. 1 is a schematic explanatory drawing which shows the overall configuration of one embodiment of an automatic incandescent lamp classification apparatus according to the invention and illustrates an example of application of a lamp classification method to judgement of the quality of incadescent lamps.

FIG. 1 is a schematic view of an embodiment in which the lamp classification method of the invention is employed to judge the quality of incandescent lamps.

An incandescent lamp 41 has, for example, a glass bulb in which a mixture consisting, by volume, of 90% of Argon gas and 10% of Nitrogen gas is sealed at a pressure of 82500 Pa (at room temperature).

A high voltage is imposed across the bulb and a filament coil (not shown) in order to produce a discharge inside incandescent lamp 41. In this embodiment, the high voltage is imposed by a high voltage generator 42 on a discharge terminal 43 that contacts the bulb. As seen in the drawing, a lamp base that is connected to the filament coil of incandescent lamp 41 contacts a ground plate 44.

On actuation of high voltage generator 42, therefore, a discharge is produced between the filament coil and discharge terminal 43.

The spectrum of light radiated during this discharge is detected by a sensor 45 which is fitted with an optical filter that passes light $\alpha$, which is in the vicinity of 560 nm, so as to permit pickup of light in a set wavelength region.

Figure 2:
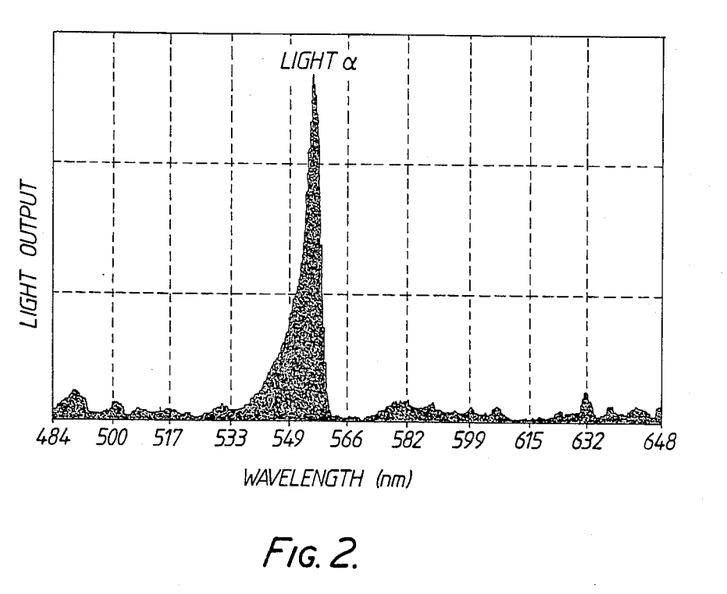
FIG. 2 shows the spectral characteristic of light in the vicinity of 560 nm that is radiated at the time of discharge.

As the result of many experiments conducted with attention focussed on the light $\alpha$ in the vicinity of 560 nm illustrated in FIG. 2 which is emitted during discharge, we discovered the following phenomenon.

FIGS. 3(a)–(e) show the timewise changes in the luminous intensity of light $\alpha$ in the vicinity of 560 nm in incandescent lamps of five grades going from good to severely defective when discharge is effected with a 50 Hz high voltage such as commercial cycle. These figures plot time on the abscissa and light $\alpha$ spectrum intensity on the ordinate. It is seen from the figures that the temporal response, i.e., the attenuation time, in the light $\alpha$ spectrum becomes shorter as products are more defective.

Figure 3:
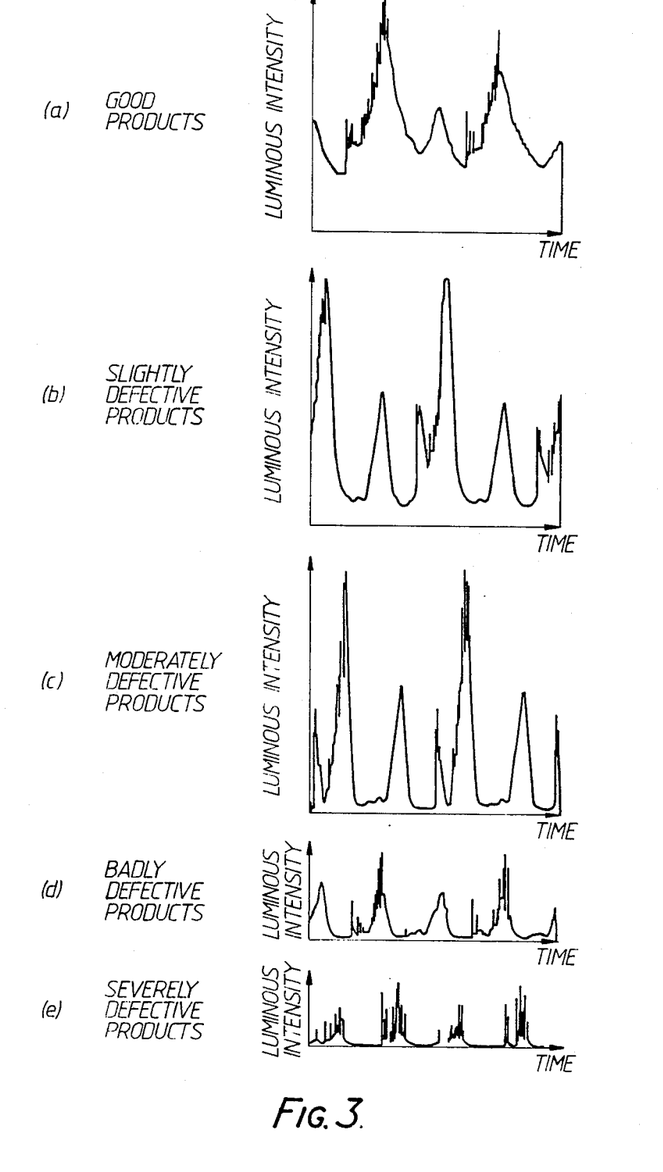
FIG. 3 shows characteristic plots indicating the timewise changes in spectral intensity in the vicinity of 560 nm in accordance with degree of defectiveness.

In other words, imposition of a high voltage results in discharge by an incandescent lamp and production of a light $\alpha$ spectrum, and the temporal response in this spectrum is very dependent on the degree of defectiveness of the lamp.

It will also be appreciated that, as shown in the figures, although there are timewise changes in the emission intensity in the light $\alpha$ spectrum (there is repeated occurrence of strong peaks and weak peaks), the form of attenuation in the spectra is one in which the strong and weak peaks coincide and are not dependent on the intensity in a spectrum. In other words, although changes in the intensity of the emitted light occurs because of variation in the discharge inside lamps, the temporal response is unaffected.

The reasons for this are largely unclear but we surmise it is due to something like the following.

It is possible that the life of particles which are in the upper state of the spectrum line is shortened due to the effects of impurities.

It is therefore possible to detect the state of gas in a lamp as regards impurities, etc. by measuring the temporal response of this light $\alpha$, i.e., the temporal amplitude of light output versus light $\alpha$ intensity.

Sensor 45 is connected via an interface 46 incorporating an integrator to a judgement device in the form of a computer 47. Interface 46 effects timewise integration and then high-speed AD conversion of the output of sensor 45. Computer 47 is constituted by a known computer and it uses the interface 46 output to calculate the attenuation time and judges the quality of a lamp from this attenuation time. The findings of judgements, etc. are displayed on the screen of a CRT display device and if a product has been judged defective a removal signal is given to a removal device not shown and the defective product is removed from the inspection line. The procedure employed in this embodiment is to calculate the light $\alpha$ attenuation time from the half-width of interface 46 output.

Figure 4:
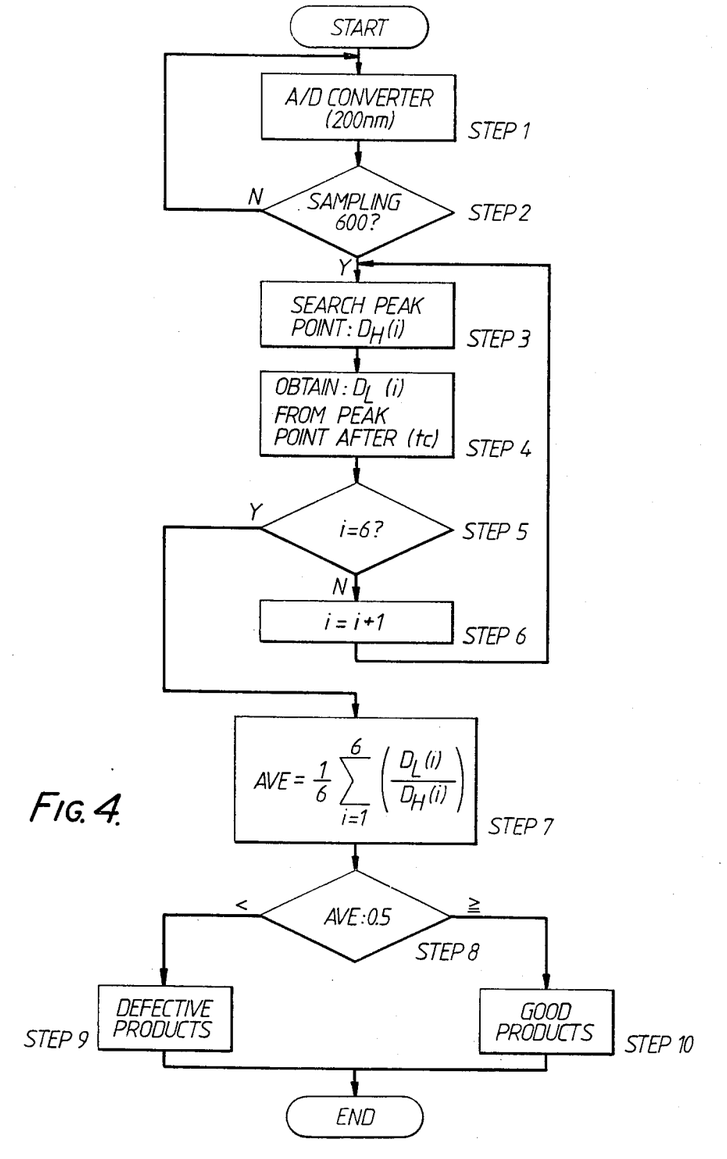
FIG. 4 shows a operational program flowchart for operating the apparatus of the invention.
Figure 5:
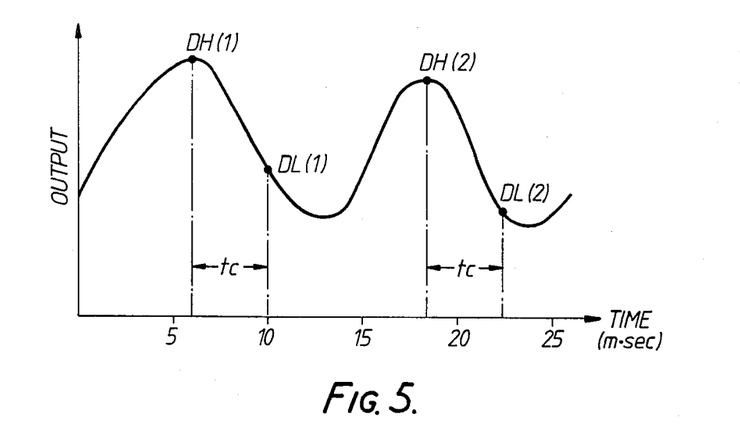
FIG. 5 and FIG. 6 are wave forms for explaining the output signal treatment.

FIG. 4 is a flowchart of a operational program suitable for controlling the automatic lamp quality judgement apparatus in which the quality of a lamp is judged by detecting the state of gas that is sealed in the lamp. Only the software routines required to implement one embodiment of the present invention are described herein. Upon beginning the flowchart at the labeled START, program control progresses through the following sequence: In Step 1, the discharge signal is sampled in a wave form with each 200 $\mu$m sec and is converted to A/D. The sampling number counts until 600 times at Step 2. If the sampling number is less than 600, the program loop backs to Step 1. This loop continues until 600 counts. If 600 data samples are obtained at Step 3, the 600 data samples are checked to determine a peak point from the wave form at DH(i) (wherein i=1, 2, . . ., n) shown FIG. 5. And in Step 4, the value of output signal DL(i) sampled after a constant time (tc) from the peak point value is detected. The constant time (tc) is set at 20 A/D converting cycles. Thus, tc=200 ($\mu$·sec)$\times$20=4.0 m·sec.

Figure 6:
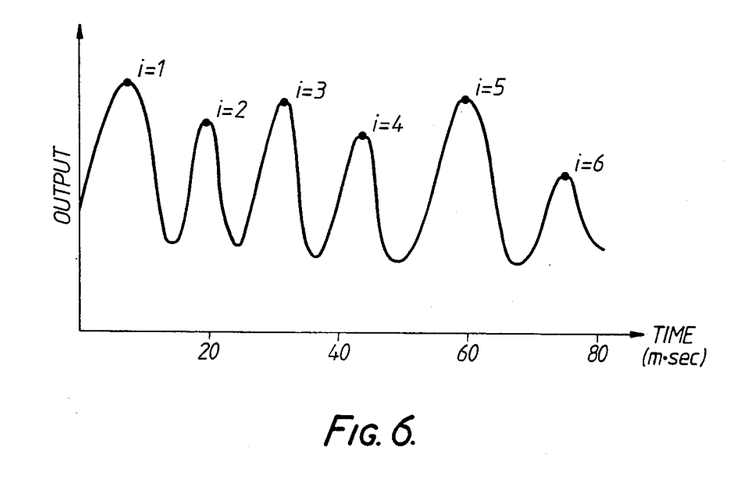

For obtaining the accuracy data, other peak points are decided, up to a number of peaks i=6. If i<6, the program executes Step 6 to return to Step 3 until i=6, as shown in FIG. 6. Next, in the Step 7, a ratio for the value at the time after the constant time tc and the peak point value is determined, and average is determined in 6 peak points. In Step 8, the value of average (AVE) is checked to determine whether or not it is greater than 0.5. If AVE<0.5, the quality of defective product is judged at Step 9. If AVE$\geq$0.6, a good product is judged at Step 10. And then the program is finished at the labeled END.

Figure 7:
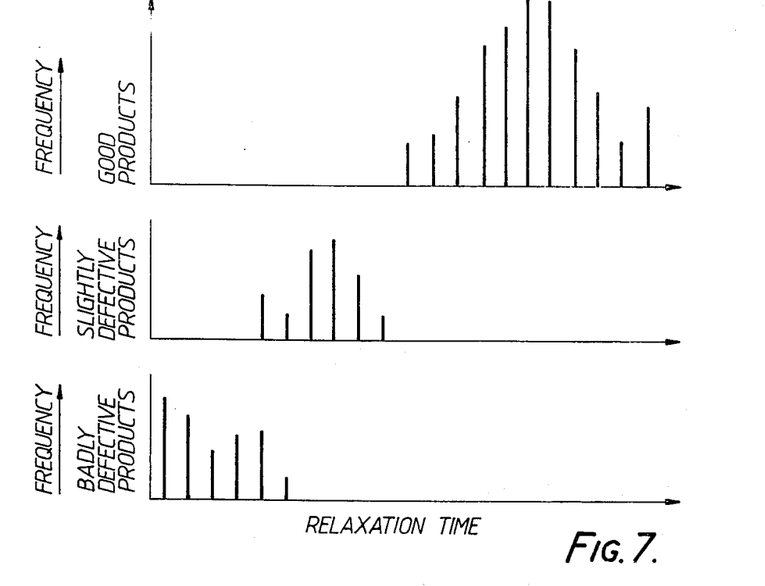
FIG. 7 is a frequency distribution plot showing the results of lamp quality classification in an embodiment of the invention.

The frequency distribution chart of FIG. 7 illustrates results of lamp quality classification by the above described embodiment, taking an abstract of the classification results for badly defective, slightly defective and good products. It is seen that the good products are practically all distributed in the region of long light α attenuation time, while the slightly defective and badly defective products are distributed in short attenuation time regions.

This indicates that lamp quality can be classified stably and with high precision on the basis of attenuation time.

The embodiment also achieves a high classification capability since the attenuation time remains unaffected even if variations in the discharge production states in lamps occur, because the portion of the spectrum of light radiated at the time of discharge that is measured is the light spectrum in the vicinity of 560 nm, for which the temporal response corresponds to the degree of defectiveness of products.

A further point is that there is no change in the attenuation time even if the light metering sensitivity of the optical sensor falls because of dirt, etc. adhering to its surface.

There is thus the very desirable feature that one has an accurate measurement parameter.

As the result of numerous and varied experiments, we discovered that peeling of an adherent film such as a silica film, etc, that is adhered to bulb inner wall surfaces can be reduced if the polarity of the high voltage imposed on lamps is such that the filament coil side is the negative electrode and the lamp bulb side is the positive electrode.

If one analyzes the spectra shown in FIG. 3 in detail, one sees that with elapse of time there is alternate production of spiky spectra and then other spectra that are about half the intensity of the spiky spectra and contain hardly any spike components.

We carried out a variety of experiments and established that peaks with no spike components are produced when electrons come out from a lamp's filament coil and that spiky peaks are produced when electrons come out from the lamp's bulb.

Production of spiky peaks is undesirable, since when they occur there can be deterioration of lamps, e.g., due to peeling of adherent films such as silica films adhered to bulb inner wall surfaces.

It is possible that what happens here is that when a large amount of electrons is supplied from a bulb wall, the supply is liable to become unstable and there is consequently simultaneous occurence of strong ion bombardment directed agains the bulb wall in order to produce sufficient excited electrons, and the result is an adverse effect on the film adhered to the bulb inner wall surface.

To reduce this strong ion bombardment, it is simply necessary to reduce the supply of electrons from the bulb side. We also found that it is still better to arrange things so that electrons are always emitted from the filament coil side. In other words, the problem can be resolved if a high voltage is imposed with the filament coil made the negative electrode and the bulb side made the positive electrode.

This can be done by, for example, imposing the high voltage on the lamp via a full wave rectifier or a half-wave rectifier. If a half wave rectifier is used, the result is imposition of a high voltage with a quiescent time corresponding to half the high voltage period and so there is more attenuation of the discharge produced in the lamp and the response time in the spectrum becomes clearer.

As well as eliminating peeling of adherent film, the above arrangement also reduces errors during input of A/D-converted data to the computer, since no spike components are input to the computer.

In addition, we achieved further improvement of reliability of the invention by including the following procedure in the above-described lamp classification method.

The procedure was to effect computation of signals of the spectrum in the vicinity of 560 nm via a limiter circuit. By way of one example of this, FIG. 8 shows signals that have been limited (been subjected to wave front restriction) to about half the intensity obtaining in the spectra of the abovedescribed embodiment shown in FIG. 3.

Figure 8:
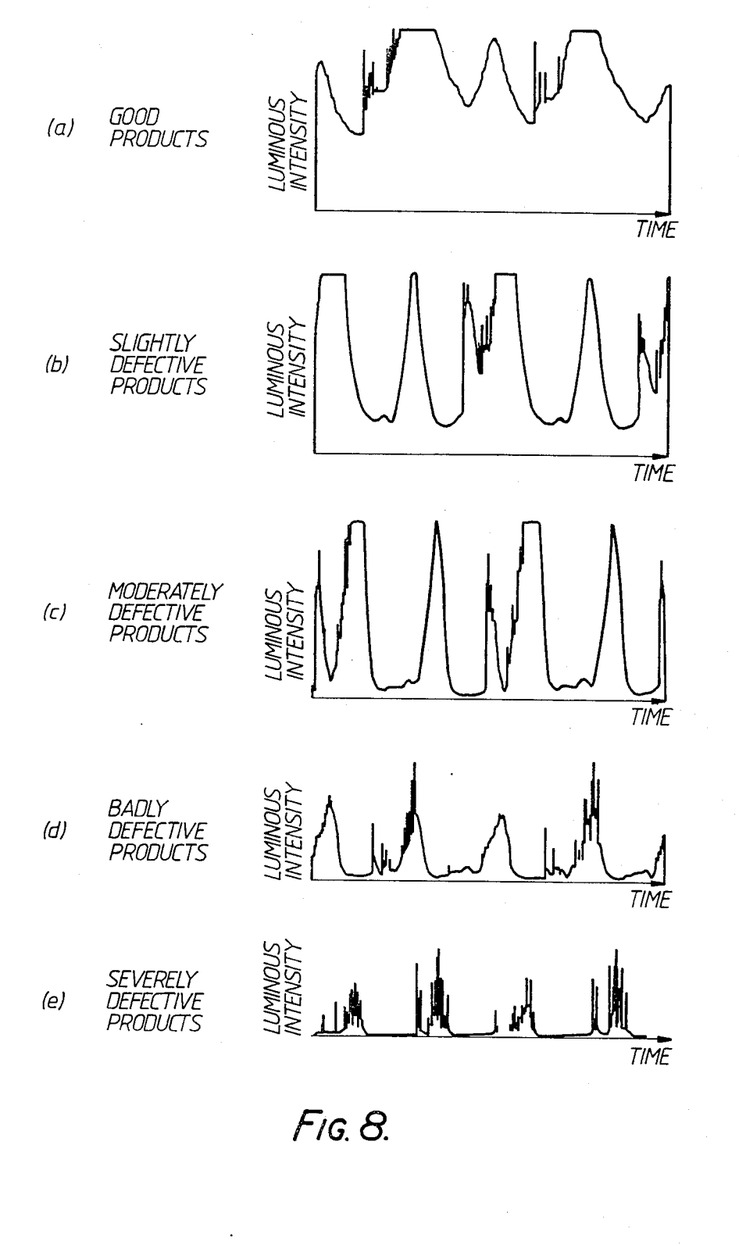
FIG. 8 shows schematic representations of signals that limit the spectra shown in FIG. 3.

It may be appreciated from FIG. 8 that one can obtain the temporal response characteristics in the spectra more clearly by timewise integration of the limited signals. To explain this in more detail, when lamps are good products the intensity in the light spectrum in the vicinity of 560 nm is large and the attenuation time is long, as noted above. Also, the intensity becomes smaller and the attenuation time becomes shorter as the quality of lamps becomes worse. Therefore, if the signals are subjected to timewise integration after they have been limited, the degree of defectiveness of lamps is clearer than it is with values of integration obtained when signals are not limited, and hence the invention is made still more reliable.

By a similar concept, instead of a limit circuit, one could, for example, make the degree of defectiveness of lamps clearer by using a logarithmic amplifier to effect logarithmic amplification of signals obtained by the sensor or effect this kind of signal processing within the computer.

We also found as the result of many experiments and much investigation that is it preferable to have a repetition frequency of 1 kHz or less.

More specifically, we found that the intensity in the light α spectrum in the vicinity of 560 nm is dependent on the repetition frequency of the imposed voltage and that differences in the intensity appear at a boundary of about 1 kHz.

Figure 9:
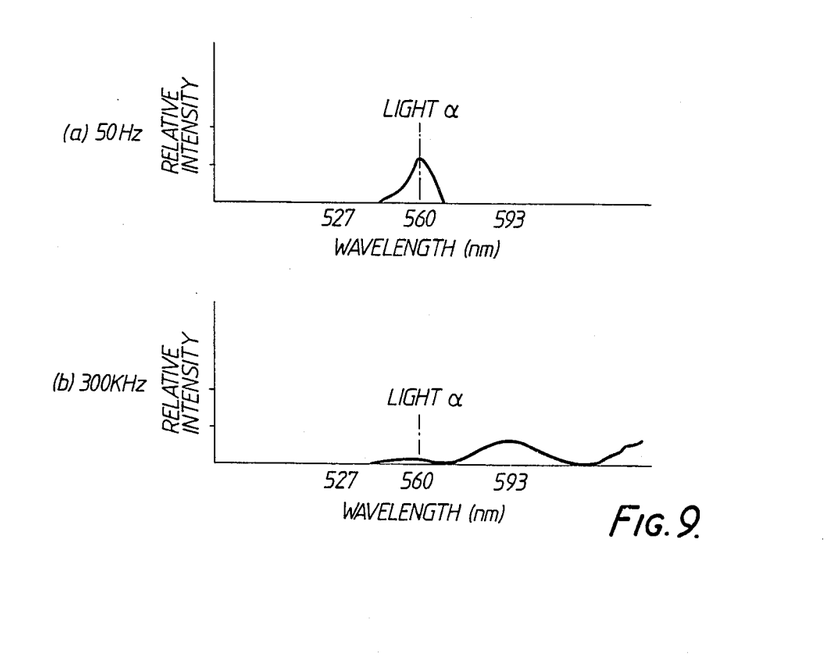
FIG. 9 shows characteristic plots of light spectrum intensities in the vicinity of 560 nm when discharge is produced by high voltages with repetition frequencies of 50 Hz and 300 kHz.

By way of one example, FIG. 9 shows the spectra in the vicinity of 560 nm when one and the same incandescent lamp is subjected to imposition of high voltage at repetition frequencies of 50 Hz and 300 kHz. It is seen from this figure that the light intensity in the vicinity of 560 nm is great in the low frequency region and becomes smaller in the high frequency region. It is surmised that the reason for this is as follows.

When the repetition frequency of the high voltage imposed on a lamp is low, it is difficult for discharge to occur, but once it does a high-speed electron stream is produced, so increasing the probability of production of light in the vicinity of 560 nm.

On the other hand, when the repetition frequency of the high voltage is high, although discharge can occur comparatively easily, the mean velocity of electrons during discharge is lower, and so there is relatively less probability of production of light in the vicinity of 560 nm.

It was found empirically that although the boundary value is affected to some extent by the sealed-in gas, etc., it is about 1 kHz.

Although the temporal response of light $\alpha$ was ascertained from integrated values or half-width values in the embodiment described above, the invention is not limited to this but it is also possible to make inferences by means of various parameters that permit the temporal response to be ascertained.

For example, one may effect timewise differentiation of signals detected by the sensor and determine the relaxation rate in their spectrum.

Further, although only light $\alpha$ is detected in this embodiment, one may, for example, use two sensors to detect light $\alpha$ and other light that is not affected by defectiveness of lamps and make a distinction between good and defective lamps on the basis of relative changes of the temporal responses of the two types of light.

Light that is unaffected to much by lamp defectiveness in the case of ordinary incandescent lamps is typically light in the vicinity of 670 nm.

There now follows a description, with reference to the drawings, of another embodiment of an automatic incandescent lamp classification apparatus according to the invention.

Figure 10:
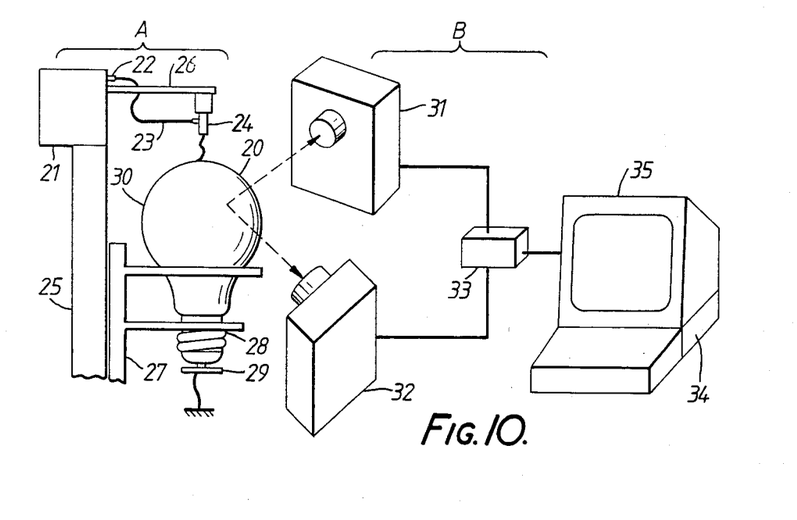
FIG. 10 is a schematic view of an example of the configuration of another embodiment of the invention.

FIG. 10 shows the overall configuration of an embodiment of the invention which comprises a discharge generator A that produces a discharge in an incandescent lamp 20 and a judgement device B.

In discharge generator A, a discharge terminal 24 is connected by a lead 23 to the output terminal 22 of a high voltage generator 21 which produces a high voltage that is alternately repeated at 50 Hz such as a commercial cycle, for example. High voltage generators 21 is set on top of a column 25 standing on a machine bed not shown and discharge terminal 24 is held suspended from an arm 26 that is made of insulating material and extends sideways from the upper end of column 25.

Incandescent lamps 20 are held by holders 27 individually provided on the machine bed not shown and are carried forward to a set inspection position below discharge terminal 24. When an incandescent lamp 20 is positioned in the detection position, its base 28 is grounded by being in electrical contact with a ground plate 29.

A mixture of, e.g., 90% Argon gas and 10% Nitrogen gas by volume is sealed inside the glass bulb 30 of incandescent lamp 20 at a pressure of 82500 Pa (at 20° C.) and a discharge is produced between a metal element in glass bulb 30 and discharge terminal 24. The spectrum of light emitted during this discharge is detected by a 1st light sensor 31 and a 2nd light sensor 32 located to the sides of the incandescent lamp 20 inspection position. 1st and 2nd light sensors 31 and 32 are installed on a machine table, etc. not shown in a manner such that, although the directions in which they receive light are different, they both receive light from the same set location inside bulb 30, as indicated by the dashed lines. 1st and 2nd light sensors 31 and 32 are provided with optical filters such that they detect light in set wavelength regions in the spectrum of light illustrated in FIG. 11 that is radiated at the time of discharge. For example, 1st light sensor 31 is fitted with an optical filter for detection of light $\alpha$ in the wavelength region in the vicinity of 560 nm and 2nd light sensor 32 with an optical filter for detection of light $\beta$ in the wavelength region in the vicinity of 670 nm.

Figure 11:
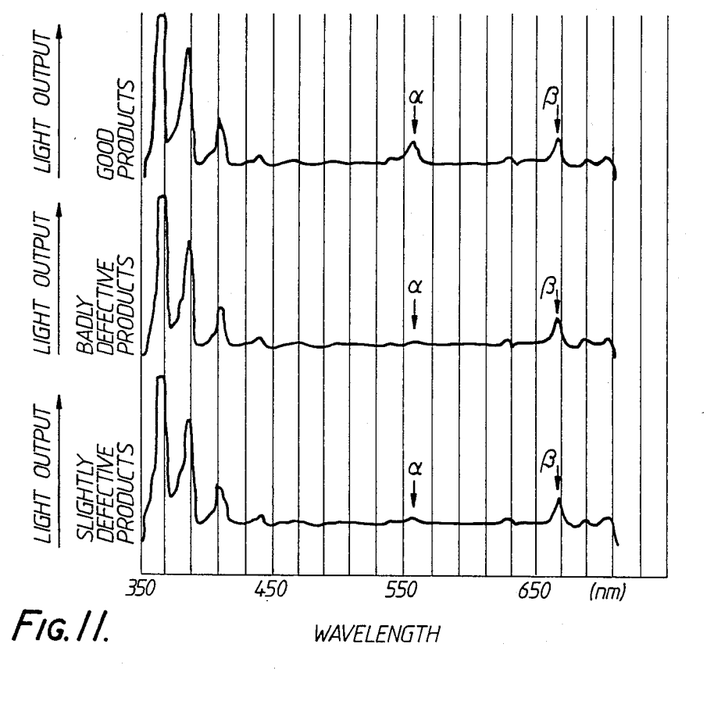
FIG. 11 is a spectral distribution plot of the spectra of light radiated for different incandescent lamp quality grades in an embodiment of the invention.

As shown in the spectral distribution plots of FIG. 11, within the spectrum of light that is radiated on discharge, when products are good the level of light $\alpha$ with a wavelength of around 560 nm is markedly different from its level in the case of badly defective products in which there is large admixture of impurities or there is a bad degree of leakage. In more detail, the light $\alpha$ output is comparatively large when products are good but becomes gradually smaller as the degree of defectiveness is greater, to become minimum for badly defective products. Thus, it is possible to judge the quality of incandescent lamp 20 solely through detection of this light $\alpha$. If, however, incandescent lamps 20 become displaced from the set inspection position, there is liable to be fluctuation and it is not possible to make an accurate classification.

On the other hand, the output of light $\beta$ with a wavelength in the vicinity of 670 nm is more or less constant, regardless of whether products are good, defective or badly defective, and when products are good, this output is at generally the same level as the light $\alpha$ output.

The light intensity ratio $\alpha/\beta$ of $\alpha$ and $\beta$ therefore constitutes a parameter for judging the quality of incandescent lamps 20, and there is the further point that even if incandescent lamps 20 are displaced from the set inspection position and fluctuation in the level both of light $\alpha$ and of light $\beta$ occurs, $\alpha/\beta$ remains more or less constant since the fluctuation affects the two types of light $\alpha$ and $\beta$ more or less equally. The fact that the intensity ratio $\alpha/\beta$ of light $\alpha$ and light $\beta$ is generally constant makes it possible to effect stable classification of quality even if there are differing states of production of discharge and fluctuations in the levels of light $\alpha$ and light $\beta$ occur due to incandescent lamps 20 being displaced from the set inspection position.

1st and 2nd light sensors 31 and 32 are connected via an interface 33 to a judgement device in the form of a computer 34 which calculates the intensity ratio $\alpha/\beta$ of light $\alpha$ and light $\beta$ and judges the quality of incandescent lamps 20 on the basis of this intensity ratio $\alpha/\beta$. Computer 34 is a known computer and it displays the findings of incandescent lamp quality judgement, etc. on the screen of a CRT display device 35, causes defective products to be removed from the inspection line by giving removal signals to a removal device (not shown) when products are judged defective and stores data relating to this in a memory section.

Figure 12:
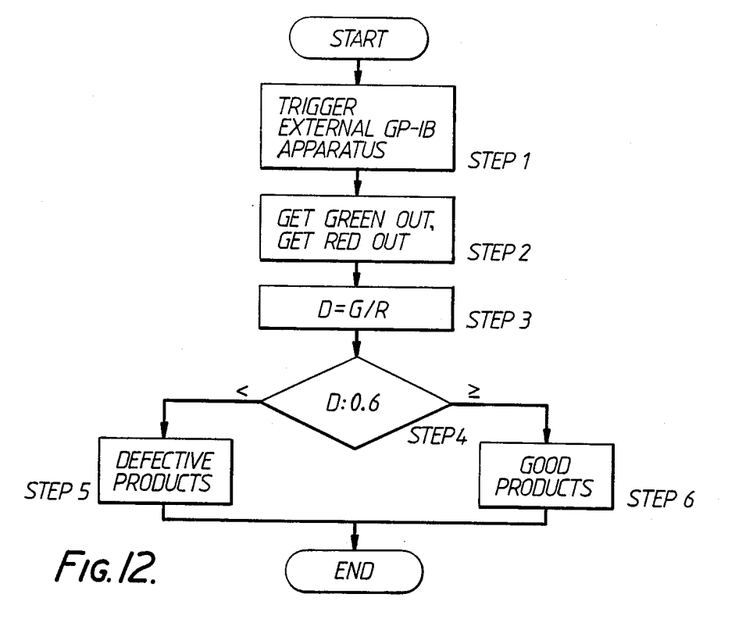
FIG. 12 shows a operational program flowchart for operating the apparatus in the another embodiment of the invention.
Figure 13:
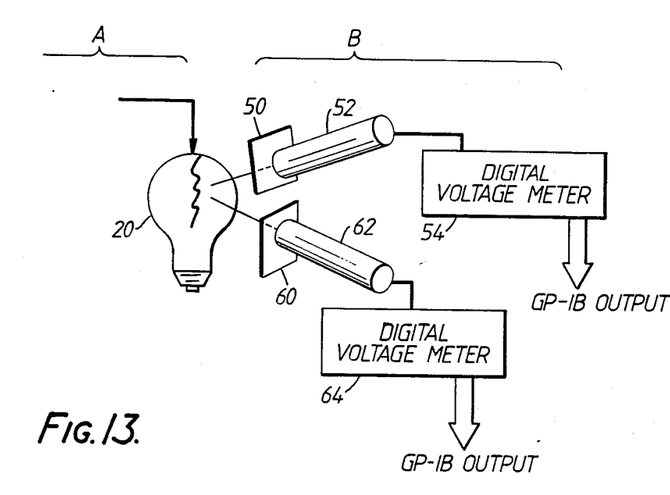
FIG. 13 is a partially schematic view of an example of the configuration of another embodiment of the invention.

The leakage judgement for each incandesent lamp is excuted according to a operational program flowchart as shown in FIG. 12. An external GP-IB apparatus is triggered by signal (Step 1). A GP-IB output signal through a digital voltage meter 54 is detected from optical sensor 52 which is detected only a light (as first light) passed the green filter 50. And at same time, another GP-IB output signal is detected by the sensor 62 through a digital voltage meter 64 as only light (as second light) passed by the red filter 60 (Step 2). A ratio D (D=G/R) of the green light output signal (=G) and red light output signal (=R) are calculated at Step 3. At Step 4, it is checked if the searched of the ratio value D is up to 0.6 or not. If D<0.6, the lamp is judged to be defective at Step 5, and if D≧0.6, the lamp is judged to be good at step 6. And the operation of the program is finished at the step labeled END.

The light $\alpha$ emission intensity for given repetition frequencies of the high voltage imposed on incandescent lamps 20 was found to be the same as the findings shown in FIGS. 9(a) and (b), and will be described with reference to these figures. FIG. 9(a) shows the case where the spectrum in the vicinity of 560 nm is enlarged when a good quality incandescent lamp is caused to produce a discharge by a high voltage at a repetition frequency of 50 Hz as in this embodiment, while FIG. 9(b) shows the case where this lamp is caused to produce a discharge by a high voltage at a repetition frequency of 300 kHz. It is seen from these figures that the intensity of light α, which varies depending on the quality of lamps, is much greater with a high voltage of 50 Hz and therefore gives a greater indication of changes in sealed-in gas caused by incandescent lamp leakage, etc. (The peaks observed in the region of wavelengths longer than 560 nm in FIG. 9(b) are probably due to differences in the discharge phenomenon caused by high frequency discharge and it was confirmed that these peaks appear regularly regardless of the quality of incandescent lamps.) We carried out similar experiments in which we effected discharge by high voltage at various frequencies and found that the emission intensity of light α resulting from high voltage in the low frequency regions tends to be stronger.

It was found that this is not only a trend that is specific to high voltage whose magnitude and polarity change with time, i.e., alternating high voltage, as in this embodiment, but that the same trend exists with so-called pulse or rectified high voltage whose magnitude changes with time.

It is possible that this phenomenon is due to the following reasons. When the repetition frequency of the high voltage imposed on a lamp is low, it is difficult for discharge to occur, but once it does a high-speed electron stream is produced, so increasing the probability of production of light α. On the other hand, when the repetition frequency of the high voltage is high, although discharge can occur comparatively easily, the average velocity can occur comparatively easily, the average velocity of electrons during discharge is lower, and so there is relatively less probability of production of light α.

It was found empirically that, although it is affected to some extent by the gas sealed in incandescent lamps, etc., this change in the phenomenon occurs at a boundary at which the high voltage repetition frequency is about 1 kHz.

We further confirmed that this phenomenon occurs on application of high voltage pulses, typically in the form of square waves or rectangular waves, etc., at a repetition frequency of 1 kHz or less.

To put things another way, at a repetition frequency of over 1 kHz, there is a greater volume of discharge and the next imposition of high voltage takes place before electrons have disappeared sufficiently, with the result that the amount of discharge current becomes greater and the electron temperature falls, and it is surmised that the probability of excitation to a higher level at which 560 nm (light α) emission occurs falls because of this.

As described above, causing discharge with a high voltage with a repetition frequency of 1 kHz or less results in markedly greater light α emission intensity and hence in much improved precision of the intensity ratio α/β which is calculated in order to judge the quality of incandescent lamps. This means the incandescent lamp classification performance is improved. More specifically, whereas the quality classification performance of the automatic incandescent lamp classification apparatus we developed earlier was about 96% or more, this embodiment gives a still better classification performance of about 98% or more.

Figure 14:
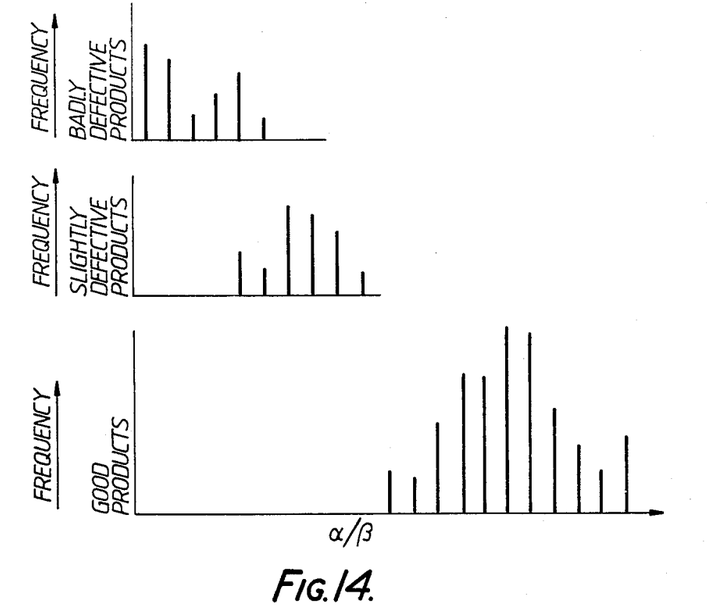
FIG. 14 is a frequency distribution plot illustrating the results of classification by the embodiment shown in FIG. 10.

Results of incandescent lamp 20 quality classification by this embodiment are illustrated in the frequency distribution plot of FIG. 14, which shows the results of classification of 150 badly defective incandescent lamp 20 products, 140 slightly defective products and 450 good products on the basis of α/β. It is seen that practically all the good products are distributed in the region in which the α/β value is large, while the distribution goes towards the regions of smaller α/β values as products become slightly defective or badly defective. In other words, it is shown that the quality of incandescent lamps 20 can be classified stably and with high precision on the basis of the value of α/β.

As it determines the intensity ratio α/β of light α in a set wavelength region and light β in another wavelength region in the spectrum of light emitted at the time of discharge, this embodiment is designed to improve the quality classification capability, because the intensity ratio α/β of the two forms of light α and β remains more or less constant even if incandescent lamps 20 are displaced from the set inspection position and differing states of production of discharge occur. For example, the various drawbacks of the conventional example using high frequency discharge shown in FIG. 15 and FIG. 16 mean that its quality classification performance is only around 70%, whereas this embodiment gives a quality classification performance of about 96% or more.

Although light α and light β are detected separately by 1st and 2nd light sensors 31 and 32 in the embodiment described above, the invention is not limited to this but the spectra of both light α and light β may, for example, be detected simultaneously by a single light sensor.

Also, although light β is set as light in the vicinity of 670 nm, the invention is not limited to this and it may be set as light in any wavelength region that is convenient for comparison with the intensity of light α.

Further, needless to say, although computer 34 is used as a judgement device, as long as it possesses a function for calculating α/β values and a function for discerning the quality of incandescent lamp on the basis of α/β values, this device need not be a computer.

What is claimed is:

1. Lamp quality judgement apparatus which detects the state of gas that is sealed in an electric lamp such as an incandescent lamp in which Argon-Nitrogen gas is sealed comprising a discharge generation device that imposes a high voltage across the bulb of a lamp in which gas and a filament coil of said lamp are sealed and causes production of a discharge in which a first light spectrum of wavelengths in a range of 550–570 nm is radiated in said lamp and a light spectrum analysis means which analyzes the state of said first light spectrum radiated by said discharge.

2. Lamp quality judgement apparatus as claimed in claim 1, wherein the repetition frequency of said discharge produced by said discharge generation device is made 1 kHz or less.

3. Lamp quality judgement apparatus as claimed in claim 1, wherein the repetition frequency of said discharge produced by said discharge generation device is made that of a commercial line frequency.

4. Lamp quality judgement apparatus as claimed in claim 3, wherein the commercial line frequency is 50 Hz.

5. Lamp quality judgement apparatus as claimed in claim 1, wherein said discharge generation device is constituted high voltage pulse generation device.

6. Lamp quality judgement apparatus as claimed in claim 5, wherein the high voltage produced by said high voltage pulse generation device is a high voltage with repeated quiescent periods.

7. Lamp quality judgement apparatus as claimed in claim 6, wherein the repetition frequency of the high voltage pulse produced by said high voltage pulse generation device is made 1 kHz or less.

8. Lamp quality judgement apparatus as claimed in claim 7, wherein the repetition frequency of the high voltage pulse produced by said high voltage pulse generation device is made 50Hz.

9. Lamp quality judgement apparatus as claimed in claim 5, wherein the high voltage pulse generation device includes terminals for imposition of a high voltage pulse on said lamp by said high voltage pulse generation device, said terminals having a polarity such that high voltage pulse imposition is effected with the filament coil constituting a negative electrode.

10. Lamp quality judgement apparatus as claimed in claim 1, wherein said light spectrum analysis means is a means which analyzes the temporal response characteristic of a light spectrum.

11. Lamp quality judgement apparatus as claimed in claim 1, wherein said light spectrum analysis means is so constituted that it effects analysis comparing the intensity of light in said first light spectrum and of light in a second light spectrum other than said first light spectrum.

12. Lamp quality judgement apparatus as claimed in claim 11, wherein said second light spectrum is light of wavelengths in a range of 660–680 nm.

13. Lamp quality judgement apparatus which comprises a discharge generation device which causes a discharge to be produced in incandescent lamps which is containing a sealed-in gas having Argon gas and Nitrogen gas as its main components by imposing a high voltage that is repeated at 1 kHz or less and a judgement device which makes a distinction between good and bad incandescent lamp products on the basis of the intensity ratio of light of at least two light spectrums constituted by light of a first light spectrum including light of wavelengths in a range of 550–570 nm that is radiated at the time of said discharge whose output is caused to vary in accordance with the state of gas in said incandescent lamp, and light of a second light spectrum in which light intensity does not vary as much as a function of the state of the gas in comparison with light of said first light spectrum.

14. Lamp quality judgement apparatus as claimed in claim 13, wherein said second light spectrum includes light of wavelengths in a range of 660–680 nm.

15. Lamp quality judgement method wherein a discharge is produced in a lamp in which gas is sealed by imposition of a voltage between a bulb and a filament coil of said lamp; and said lamp is judged a good product or a bad product on the basis of the temporal response characteristic in a light spectrum of wavelengths in a range of 550–570 nm.

16. Lamp quality judgement method as claimed in claim 15, wherein the polarity of said voltage imposed on said lamp in order to produce said discharge is such that said filament coil constitutes a negative electrode.

17. Lamp quality judgement method as claimed in claim 15 or claim 16, wherein said voltage imposed on said lamp in order to produce said discharge is repeated at a frequency of 1 kHz or less.

* * * * *